(12) United States Patent  
Hilton (10) Patent No.: US 8,827,215 B2  
(45) Date of Patent: Sep. 9, 2014

(54) SYSTEMS AND METHODS FOR SECURING MOBILE MEDICAL EQUIPMENT SUPPORTER SYSTEMS TO PATIENT TRANSPORTERS

(76) Inventor: Randall D. Hilton, Castro Valley, CA (US)

( * ) Notice: Subject to any disclaimer, the term of this patent is extended or adjusted under 35 U.S.C. 154(b) by 354 days.

(21) Appl. No.: 13/225,091

(22) Filed: Sep. 2, 2011

(65) Prior Publication Data

US 2013/0055542 A1    Mar. 7, 2013

(51) Int. Cl.
*F16L 3/00* (2006.01)
*A61G 7/05* (2006.01)
*B23P 11/02* (2006.01)
*F16B 7/04* (2006.01)
*A61G 12/00* (2006.01)
*F16B 2/12* (2006.01)
*F16B 2/10* (2006.01)

(52) U.S. Cl.
CPC ............. *A61G 7/0503* (2013.01); *F16B 7/0486* (2013.01); *A61G 12/008* (2013.01); *A61G 2203/80* (2013.01); *F16B 2/12* (2013.01); *F16B 2/10* (2013.01)
USPC ............................................. 248/121; 29/453

(58) Field of Classification Search
USPC .................. 29/428, 453, 559; 248/121, 122.1, 248/125.8; 403/345; 280/35
See application file for complete search history.

(56) References Cited

U.S. PATENT DOCUMENTS 7,845,601 B1 *    12/2010  Culpepper et al. ......... 248/125.2
2005/0150851 A1 *  7/2005  Norris ........................... 211/107

* cited by examiner

*Primary Examiner* — John C Hong
(74) *Attorney, Agent, or Firm* — Kang S. Lim (57) ABSTRACT

The present invention relates to systems and methods for securing a mobile medical equipment supporter system, such as an infusion pump pole, to a mobile patient transporter, such as a gurney, thereby enhancing patient and attendant safety. The supporter system includes a primary support structure, one or more attachment points configured to secure medical delivery device(s) and/or medical monitoring device(s), a wheeled mobility assembly, and a hitcher assembly having a hitcher coupler configured to operatively mate with a corresponding hitchee coupler of the mobile patient transporter. In some embodiments, the mobility assembly includes a carousel with three or more rotatably attached wheeled extensions. The coupling process starts by decreasing the height of the patient transporter. Next, the hitcher coupler is aligned to the hitchee coupler. The hitcher coupler is then secured to the hitchee coupler by increasing the height of the patient transporter, thereby enabling the patient transporter to be propelled without a need to separately propel the supporter system. The supporter system footprint can also be reduced by further increasing the height of the patient transporter, thereby enhancing maneuverability.

6 Claims, 8 Drawing Sheets

SYSTEMS AND METHODS FOR SECURING MOBILE MEDICAL EQUIPMENT SUPPORTER SYSTEMS TO PATIENT TRANSPORTERS

BACKGROUND

The present invention relates to systems and methods for securing a mobile medical equipment supporter system, such as an infusion pump pole, to a mobile patient transporter, such as a gurney, thereby enhancing patient and attendant safety and convenience.

In a healthcare provider environment, it is common for a patient to be attached to an intravenous (IV) line and often also attached to the leads of one or more monitoring devices. The patient is typically resting on a rollable bed or gurney or seated on a wheelchair for their safety or out of necessity.

Generally in the case of a bed or gurney, for safety reasons, two attendants, typically aides or nurses, with one attendant positioned at each end, guide and propel the bed or gurney from one location to another location, for example, from the operating recovery room to the patient's room. Often, the attendant at the head of the bed or gurney may also be responsible for guiding and propelling a mobile infusion pump pole supporting the IV line, leaving only one hand to push and guide the bed. As a result, the safety of both the patient and/or the attendants is potentially compromised by increasing the risk of collisions and/or tipping over the mobile infusion pole.

Similarly, when a patient is in a wheelchair and also coupled to an IV line and/or a monitoring device, instead of a single attendant responsible for pushing the wheelchair, two attendants are now probably required; with one attendant responsible for propelling the wheelchair, and the second attendant responsible for propelling the mobile infusion pump pole.

It is therefore apparent that an urgent need exists for systems and methods for operatively coupling a mobile medical equipment supporter system to a mobile patient transporter. This improved coupling enables attendants to safely and efficiently transport patients from one location to another in healthcare provider settings.

SUMMARY

To achieve the foregoing and in accordance with the present invention, systems and methods for securing a mobile medical equipment supporter system to a mobile patient transporter is provided. In particular, a hitcher coupler and a hitchee coupler are provided for securing a mobile medical supporter system to a mobile patient transporter thereby enhancing patient and attendant safety and convenience.

In one embodiment, the supporter system includes a substantially vertical primary support structure, one or more attachment points configured to secure medical delivery device(s) and/or medical monitoring device(s), a wheeled mobility assembly, and a hitcher assembly having a hitcher coupler configured to operatively mate with a corresponding hitchee coupler of the mobile patient transporter. The hitcher coupler can be male and the corresponding hitchee coupler can be female, and both the hitcher coupler and the hitchee coupler can have circular cross-sectional profiles. In some embodiments, the mobility assembly includes a carousel and three or more wheeled extensions rotatably attached to the carousel.

The coupling process starts by increasing the relative height between the supporter system and the patient transporter. Next, the hitcher coupler of the supporter system is aligned to the hitchee coupler of the patient transporter along a substantially vertical axis. The hitcher coupler is then securely engaged to the hitchee coupler by decreasing the relative height between the supporter system and the patient transporter, thereby enabling the patient transporter to be propelled without a need to separately propel the supporter system.

In some embodiments, increasing the relative height includes lowering the height of the patient transporter, and engaging the hitcher coupler to the hitchee coupler includes raising the height of the patient transporter. The footprint of the supporter system can also be reduced by further increasing the height of the patient transporter, thereby enhancing maneuverability.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

The present invention relates to systems and methods for securing a mobile medical supporter system to a mobile patient transporter thereby enhancing patient and attendant safety and convenience.

Figure 1:
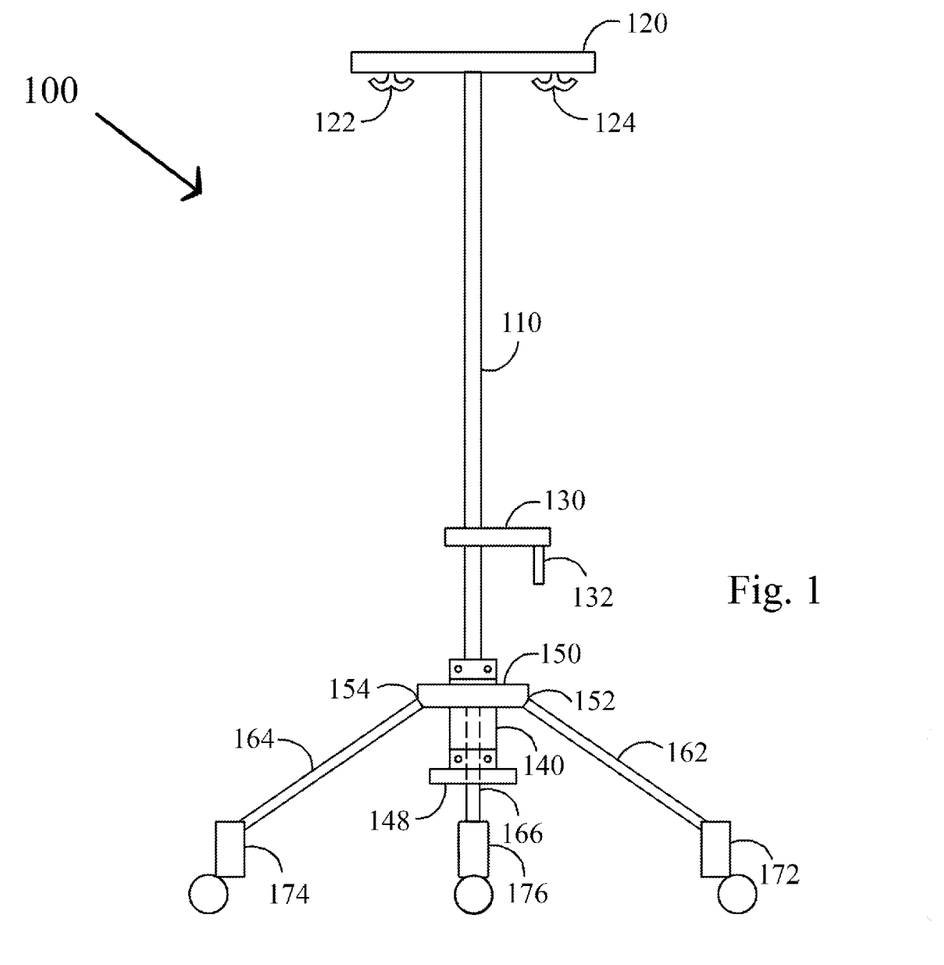
FIG. 1 is a front view of one embodiment of a mobile medical equipment supporter system configured to couple with a patient transporter in accordance with the present invention.

To facilitate discussion, FIG. 1 illustrates one embodiment of a mobile medical equipment supporter system 100 in accordance with the present invention. Supporter system 100 includes a substantially vertical primary support structure 110, an attachment bar 120, a hitcher assembly 130, a supporter base 140 with a base plate 148, a mobility assembly with a carousel 150 and three or more legs 162, 164, 166 attached to castor wheels 172, 174, 176, respectively.

Attachment bar 120 includes one of more attachment points 122, 124. Each attachment point is configured to support one or more medical delivery devices such as an IV pouch and/or one or more medical monitoring devices, such as a heart rate monitor and/or a BP monitor.

Figure 2:
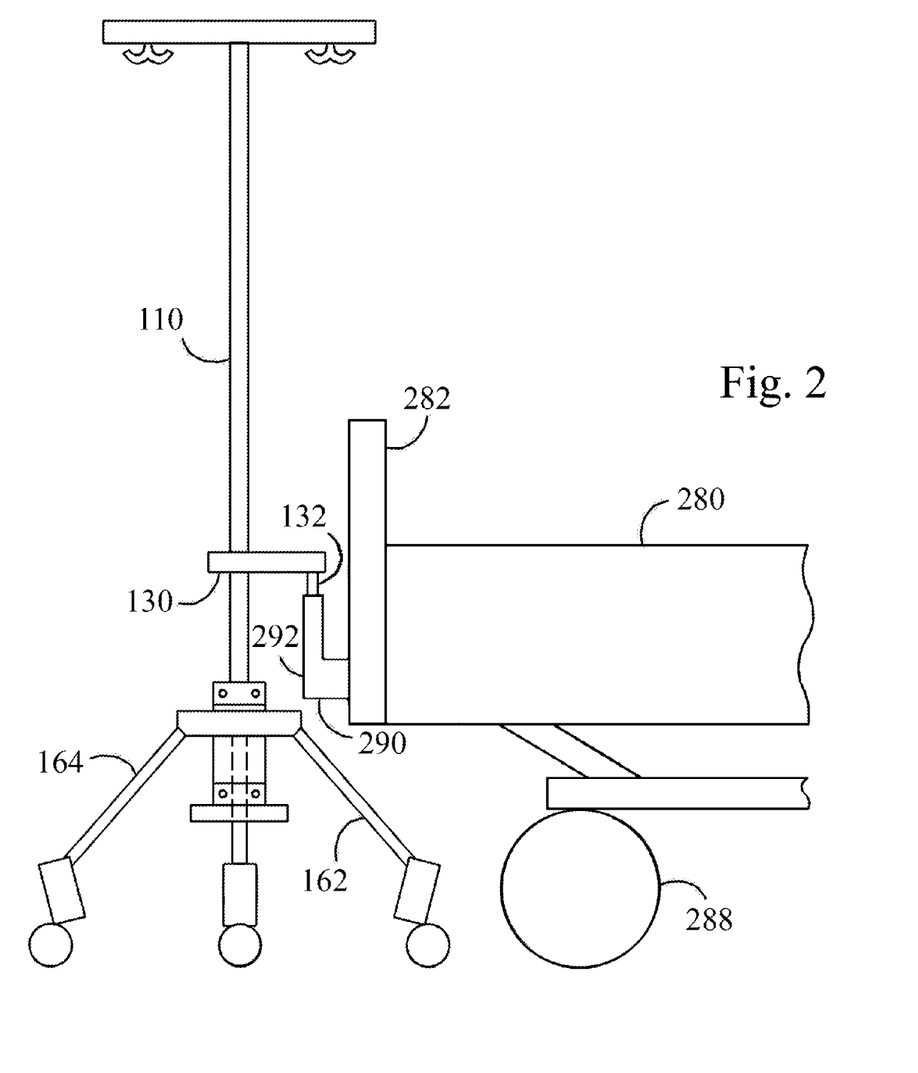
FIG. 2 shows the embodiment of FIG. 1 coupled to one end of a patient transporter.

Hitcher assembly 130 includes a hitcher coupler 132 configured to operatively couple the supporter system 100 to an existing or retrofitted hitchee coupler 292 attached to one end of a mobile patient transporter 280 as shown in FIG. 2.

Carousel 150 includes corresponding slots with pivot pins (not shown) at leg pivoting locations, e.g., pivot locations 152, 154, for supporting rotatable legs 162, 164. While these three legs 162, 164, 166 should provide sufficient stability for many applications and environments, increasing the number of legs, e.g., to six legs, should increase stability substantially by increasing the number of contact points with the ground and also by lowering the center of gravity of supporter system 100.

Referring again to FIG. 2, mobile supporter system 100 is operatively coupled to a headboard 282 of a patient transporter 280. This is accomplished by coupling hitcher coupler 132 of hitcher assembly 130 to a corresponding tubular hitchee coupler 292 of hitchee assembly 290.

Figure 3:
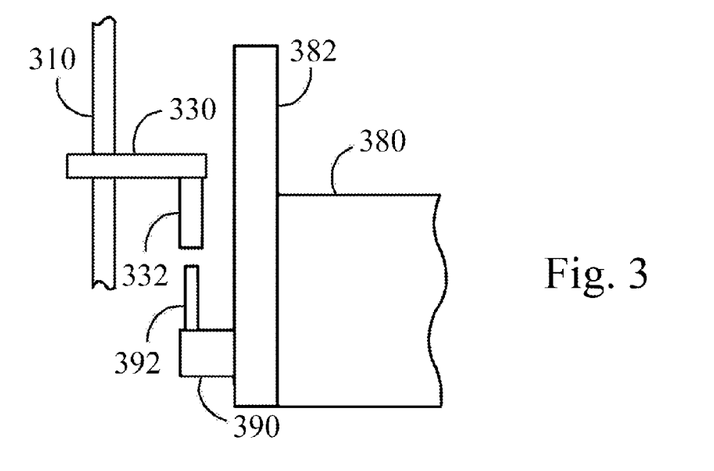
FIG. 3 illustrates a portion of another embodiment of a mobile medical equipment supporter having a hitcher coupler configured to operatively mate with a patient transporter, wherein the hitcher coupler is female and the hitchee coupler is male.

Note that although in the above-described example, hitcher coupler 132 is male and hitchee coupler 292 is female, the reverse configuration is also possible, i.e., wherein hitcher coupler 332 is female (e.g., tube-shaped) and hitchee coupler 392 is male (e.g., rod-shaped) as shown in FIG. 3.

In this embodiment, as discussed above, legs 162, 164, 166 can independently pivot like a hinge at the respective pivoting locations of carousel 150, allowing equipment supporter system 100 to be raised and lowered vertically while maintaining contact between wheels 172, 174, 176 with the ground, thereby substantially reducing the risk of tipping supporter system 110. Similarly, in most embodiments, for attendant and patient safety reasons, the height of patient transporter 280 can be raised and lowered, e.g., via a hydraulically and/or mechanically assisted system (not shown).

Accordingly, coupling of hitcher coupler 132 to hitchee coupler 292 can be accomplished efficiently and quickly in the following manner. Patient transporter 280 is lowered so that the height of the opening of hitchee coupler 292 is below that of the tip of hitcher coupler 132. The equipment supporter system 100 can now be wheeled so that hitcher coupler 132 and hitcher coupler 292 are aligned in the vertical axis. Hitchee coupler 292 can now be mated with hitcher coupler 132 by raising patient transporter 280. It is possible to reduce the footprint of supporter system 100 by raising the patient transporter 280 further so that the legs 162, 164, 166 are pivoted inwards, e.g. reducing the overall leg spread from about 22 inches to about 16 inches, thereby improving the maneuverability characteristics of the transporter 280 and supporter system 100 combination through hallways and entryways.

Similarly, during the decoupling process, the patient transporter 280 can be lowered to clear the hitchee coupler 292 from hitcher coupler 132, while lowering equipment supporter system 100 back into its spread-leg position and separating supporter system 100 from the patient transporter 280.

It may also be possible to engage equipment supporter system 100 with patient transporter 280, by vertically raising and then lowering supporter system 100, thereby inserting hitcher coupler 132 into hitchee coupler 292. Similarly, during the decoupling process, the supporter system 100 is raised vertically to clear the hitcher coupler 132 from hitchee coupler 292 and then lowered back into its full spread-leg position, thereby separating supporter system 100 from the patient transporter 280. Ideally, attendant safety can be enhanced by provided supporter system 100 with hydraulic and/or mechanical assistance during the raising and lowering of system 100.

Alternatively, in other embodiments, instead of securing hitcher assembly 130 at a fixed location on primary support structure 110, hitcher assembly 130 is configured to slide along support structure 110, thereby simplify the leg design, since legs 162, 164, 166 will no longer need to pivot during the coupling and decoupling processes. Instead, once the hitcher coupler 132 is inserted into hitchee coupler 292, hitcher assembly 130 can be secured at a desired height on support structure 110.

Several modifications can also be made to aid in the coupling process between hitcher assembly 130 and hitchee assembly 290. For example, the end of male hitcher coupler 132 can be a ball-end and/or the opening of female hitchee coupler 292 can be chamfered.

Figure 4:
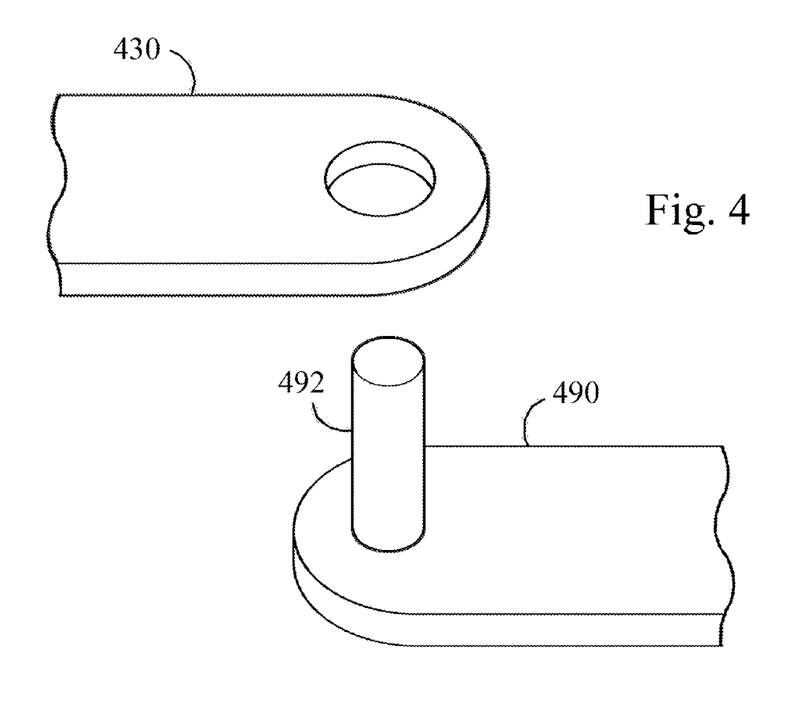
FIG. 4 illustrates yet another embodiment wherein the hitcher coupler is female and a hitchee coupler is male.

Other modifications are also possible. As shown in FIG. 4, hitcher assembly 430 can be a plate with a round hole serving as a hitcher coupler, while hitchee assembly 490 can include a rod-shaped hitchee coupler 492. Assuming that the supporter system is stable, such a system will permit a limited amount of relative horizontally movement between the supporter system 100 and the patient transporter 280, e.g., when travelling up or down a ramp.

Figure 5:
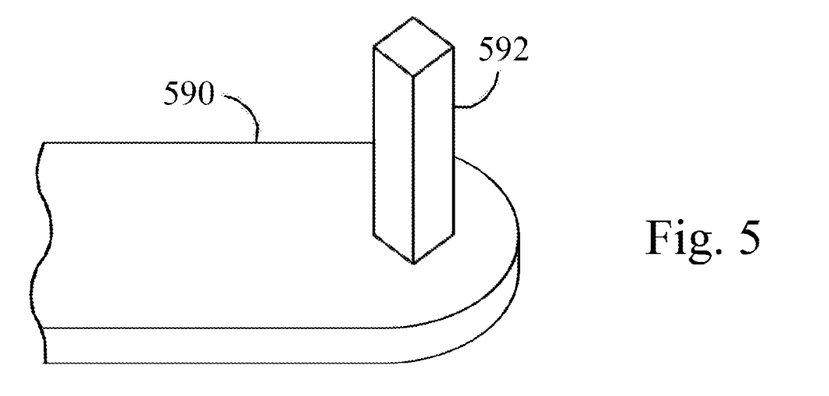
FIGS. 5 and 6 are bottom views of additional embodiments of hitcher couplers with cross-sectional profiles that are polygonal.
Figure 6:
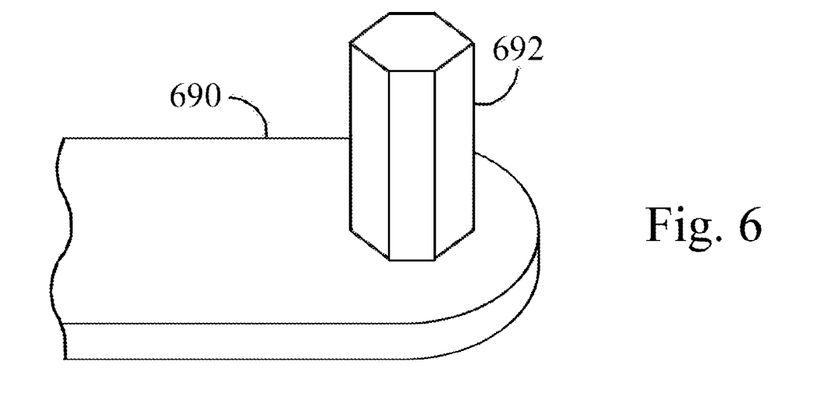

Additional modifications contemplated are illustrated by FIGS. 5 and 6, which are bottom views of alternate embodiments of hitcher/hitchee assemblies for mobile supporter systems. For example, by substituting the circular cross-sectional hitcher coupler 132 with a square cross-sectional hitcher coupler 592, and with a square cross-sectional profile change to a corresponding female hitchee coupler (not shown), rotation of the supporter system 100 relative to the patient transporter 280, (with respect to the vertical axis relative to the ground) is inhibited and may be desirable in some implements or environments.

The same rotational inhibition can also be accomplished by substituting the circular cross-sectional hitcher coupler 132 with a hexagonal cross-sectional hitcher coupler 692 paired with a corresponding hexagonal cross-sectional female hitchee coupler (not shown). Other cross-sectional profiles may also be possible including rounded-shapes such as ovals and ellipses, and polygons such as pentagons and octagons. Hence, advantages of using a non-rounded cross-section includes limited swaying or fish-tailing of the supporter system 100 thereby improving stability as the patient transporter 280 is propelled from one location to another, especially when travelling on an incline.

Figure 7:
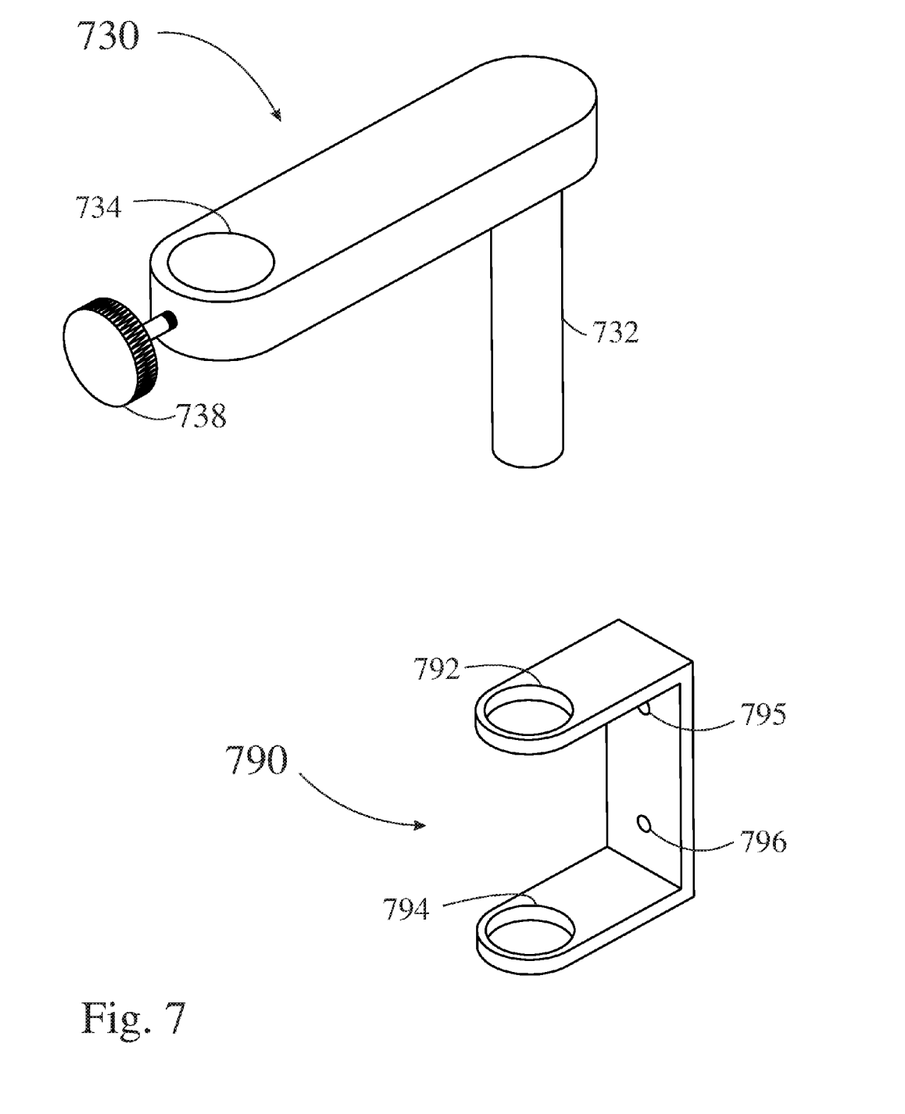
FIG. 7 is an isometric view showing an embodiment of corresponding hitcher assembly and hitchee assembly, suitable for retrofitting a conventional mobile medical supporter system and an incompatible patient transporter, respectively.

Referring to FIG. 7, it is also possible to adapt a conventional supporter system such as an infusion pump transport pole (not shown) and/or an incompatible patient transporter such as a rollable bed (not shown) by attaching retrofit hitcher assembly 730 to a main support structure of the conventional supporter system and attaching a retrofit hitchee assembly 790 to the previously incompatible patient transporter. This is accomplished by inserting the main support structure of the supporter system into the through-hole 734, and securing the hitcher assembly 730 by tightening the screw of threaded knob 738. In addition, an incompatible patient transporter can also be retrofitted by mounting hitchee assembly 790 at the appropriate location of the transporter using mounting screw holes 795, 796.

Figure 8:
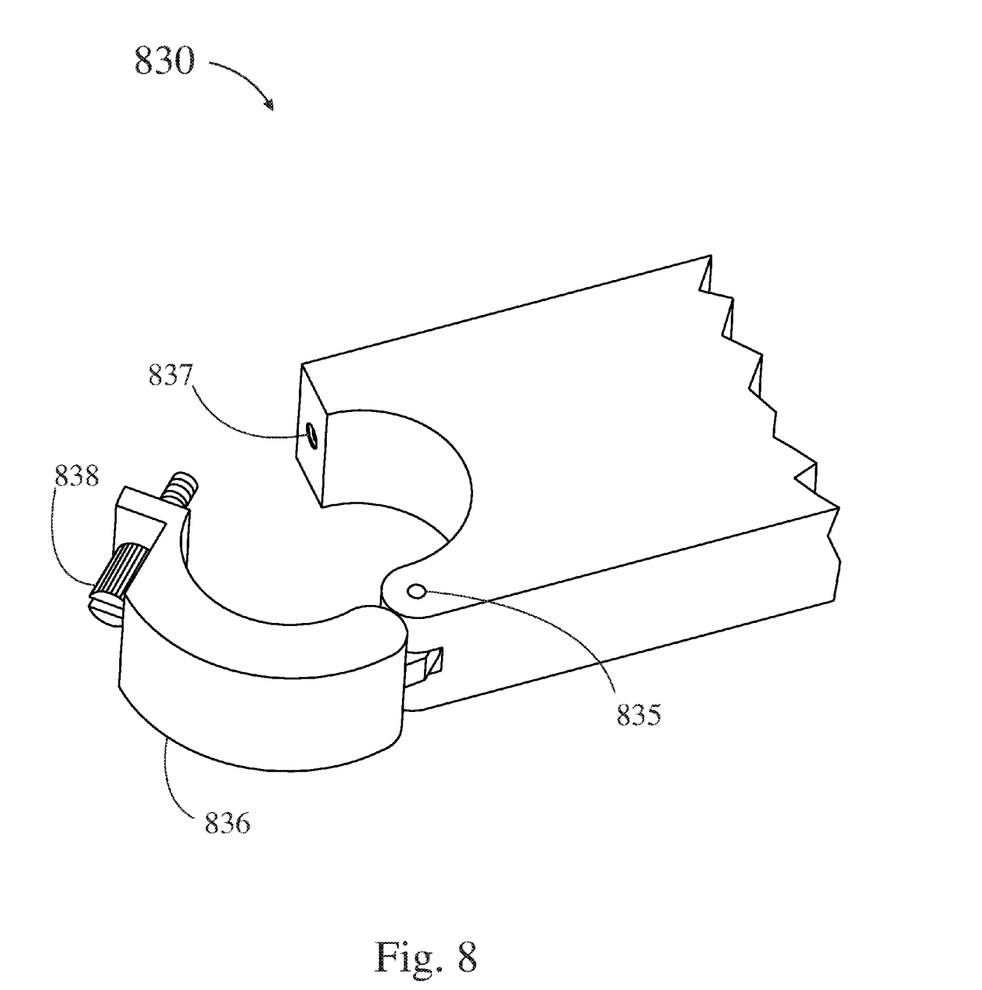
FIG. 8 shows a portion of yet another embodiment of a hitcher assembly having a clamping attachment for attaching to a mobile medical supporter system.

Alternatively, an exemplary clamp-like attachment as shown in FIG. 8 enables a hitcher assembly 830 to be easily attached to and detached from a mobile medical equipment supporter system (not shown). Such a hitcher assembly 830 is secured by (closing) pivoting the clamping ring 836 about pivot pin 835, inserting thumb screw 838 into a threaded hole 837, and tightening the resulting structure around a main support structure of supporter system.

Figure 9:
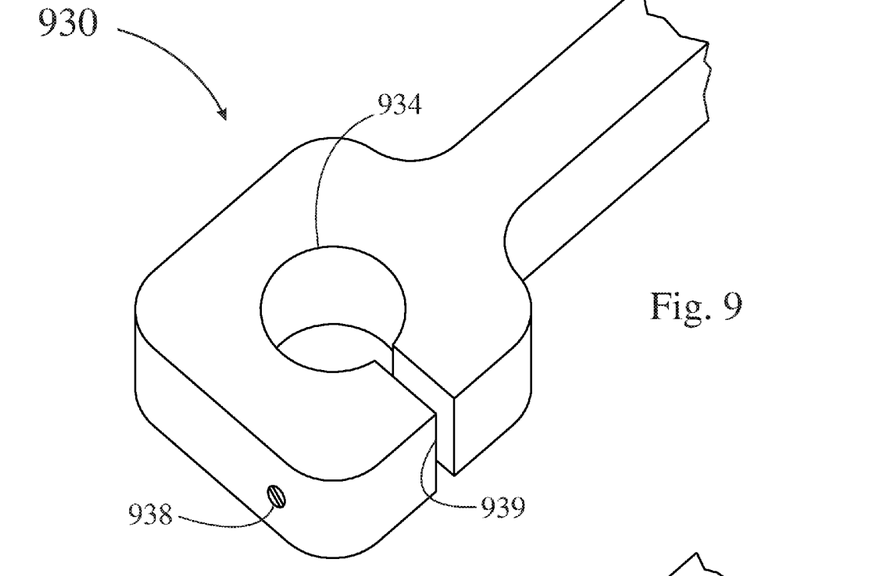
FIGS. 9 and 10 show portions of two additional embodiments of hitcher assemblies suitable for attaching to mobile medical supporter systems.

FIG. 9 shows a portion of an additional embodiment of a hitcher assembly 930 configured to be attached to a mobile medical equipment supporter system such as an infusion pump transport pole (not shown). This is accomplished by inserting the main support structure of the mobile medical support system into the split-ring 934, and securing the hitcher assembly 930 by tightening a screw 938 thereby narrowing the gap 939 and thereby reducing the circumference of the split-ring 934.

Figure 10:
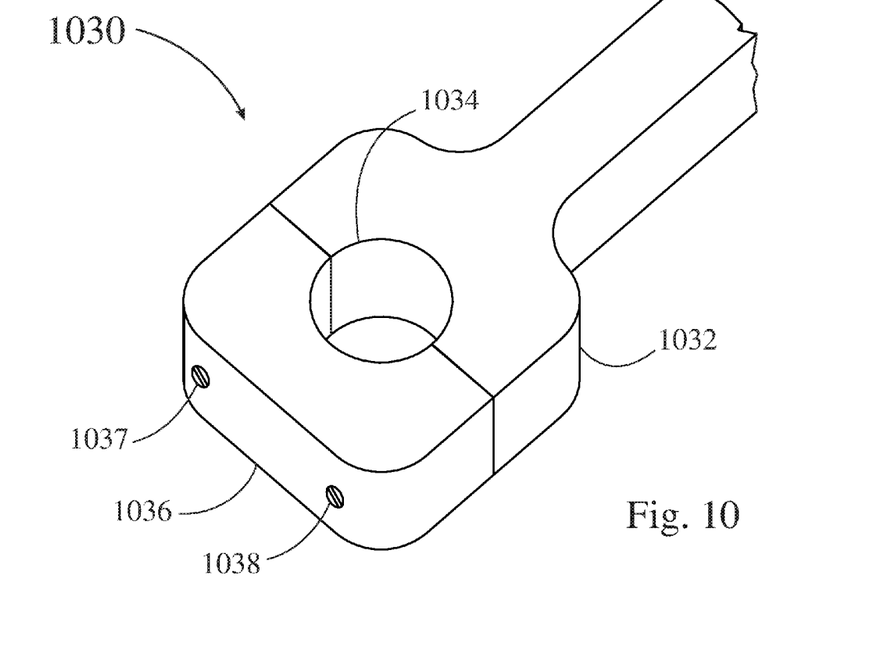

Referring now to FIG. 10, is yet another embodiment of a hitcher assembly 1030 suitable for attaching to a mobile medical supporter system (not shown). In this embodiment, the hitcher assembly is coupled to the main support structure by securing both halves of the semi-circle 1034 around the primary support structure, e.g., the pole, and then tightening screws 1037, 1038.

Figure 11:
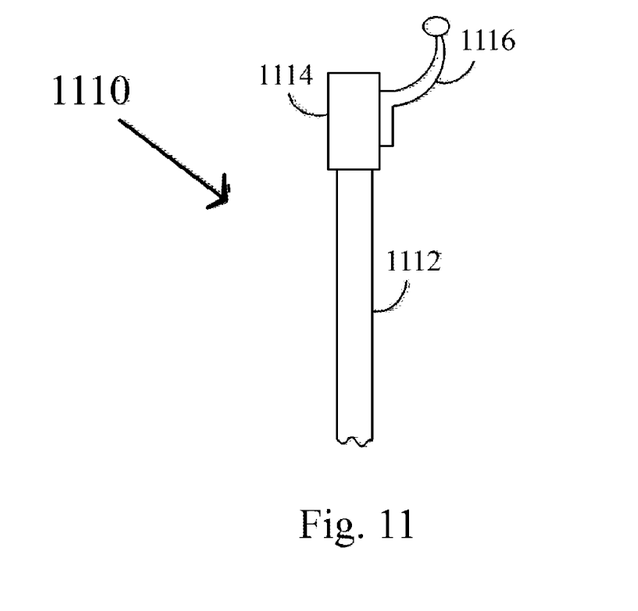
FIGS. 11 and 12 are a side view and a front view, respectively, showing additional embodiments of attachment points suitable for the supporter system of FIG. 1.
Figure 12:
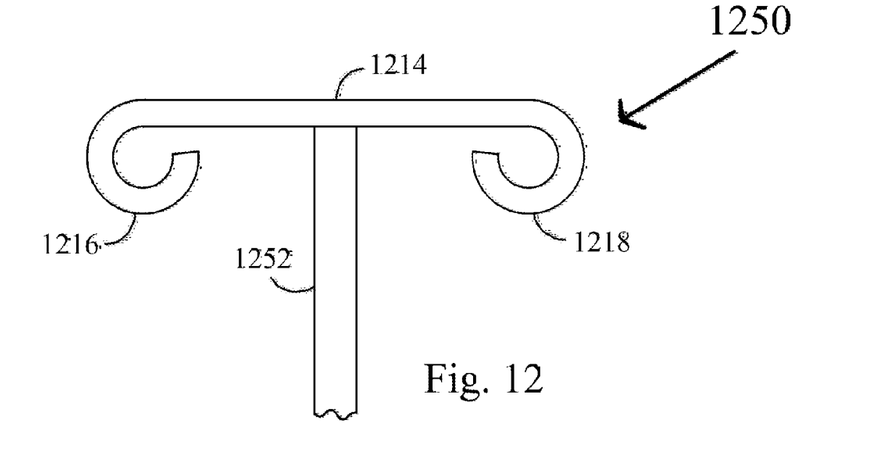

FIG. 11 is a side view showing an alternate embodiment of an attachment bar 1114 with one or more attachment point 1116, suitable for the mobile medical equipment supporter system 100. Similarly, FIG. 12 is a front view showing yet additional embodiment of an attachment bar 1214 with integral attachment points 1216, 1218 suitable for supporter system 100.

Other modifications are also contemplated in accordance with the present invention. For example, in some light-weight implementations, assuming hitcher coupler 132 can provide sufficient vertical stability via relying on the stability of hitchee coupler 292, it may be possible to provide mobility to a supporter system by using a single wheel positioned substantially underneath the main support structure. It is also possible to add hydraulics or springs to the main support structure to reduce the effort required to raise the mobile supporter system during the coupling and decoupling processes.

Further, in order to reduce the risks of unintentional decoupling of the supporter system 100 from the patient transporter 280, it is also possible, for example, to add spring-loaded ball detents to the hitcher coupler 132. Other possible "locking" techniques include ball detent pins and spring cotter pins.

While this invention has been described in terms of several embodiments, there are alterations, modifications, permutations, and substitute equivalents, which fall within the scope of this invention. Many of these modifications can also be practiced alone or in different combinations.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A mobile medical equipment supporter system for supporting a medical delivery device or a medical monitoring device for a patient, the supporter system useful in association with a mobile patient transporter for the patient, the medical equipment supporter system comprising:
   a substantially vertical primary support structure;
   at least one attachment point configured to secure at least one medical delivery device or medical monitoring device;
   a hitcher assembly having a hitcher coupler configured to operatively mate with a corresponding hitchee coupler of a hitchee assembly attached to a mobile patient transporter configured to transit on a surface; and
   a wheeled mobility assembly having a carousel and at least three wheeled extensions, and wherein at least one of the at least three wheeled extensions is operatively coupled to the carousel and configured to enable the at least one wheeled extension to articulate relative to the carousel and enabling the at least one wheeled extension to maintain substantial contact with the surface thereby enhancing stability with respect to the mobile patient transporter.

2. The medical equipment supporter system of claim 1 wherein the at least one of the at least three wheeled extensions is rotatably attached to the carousel thereby enabling footprint reduction of the medical equipment supporter system.

3. The medical equipment supporter system of claim 1 wherein the least one attachment point is part of an extension bar coupled to the primary support structure.

4. The mobile medical supporter system of claim 1 wherein the hitcher coupler is male and the hitchee coupler is female.

5. The mobile medical supporter system of claim 1 wherein both the hitcher coupler and the hitchee coupler have circular cross-sectional profiles.

6. The mobile medical supporter system of claim 1 wherein both the hitcher coupler and the hitcher coupler have polygonal cross-sectional profiles.

* * * * *